United States Patent
Bidra

(10) Patent No.: US 10,383,708 B2
(45) Date of Patent: Aug. 20, 2019

(54) ANALOGS FOR DENTAL RESTORATIONS

(71) Applicant: University of Connecticut, Farmington, CT (US)

(72) Inventor: Avinash S. Bidra, Farmington, CT (US)

(73) Assignee: University of Connecticut, Farmington, CT (US)

(*) Notice: Subject to any disclaimer, the term of this patent is extended or adjusted under 35 U.S.C. 154(b) by 8 days.

(21) Appl. No.: 15/634,374

(22) Filed: Jun. 27, 2017

(65) Prior Publication Data

US 2017/0367795 A1    Dec. 28, 2017

Related U.S. Application Data

(60) Provisional application No. 62/355,529, filed on Jun. 28, 2016.

(51) Int. Cl.
*A61C 8/00*     (2006.01)
*A61C 13/00*    (2006.01)

(52) U.S. Cl.
CPC ........ *A61C 8/0001* (2013.01); *A61C 13/0003* (2013.01)

(58) Field of Classification Search
CPC .............................. A61C 8/0001; A61C 13/34
See application file for complete search history.

(56) References Cited

U.S. PATENT DOCUMENTS

| | | | | |
|---|---|---|---|---|
| 4,955,811 A * | 9/1990 | Lazzara | ................ | A61C 8/0001 433/173 |
| 6,382,977 B1 * | 5/2002 | Kumar | ................. | A61C 8/0001 433/173 |
| 6,540,514 B1 * | 4/2003 | Falk | ..................... | A61C 8/0001 433/172 |
| 7,204,692 B2 * | 4/2007 | Klardie | ................ | A61C 8/0001 433/173 |
| 7,887,327 B2 * | 2/2011 | Marotta | ................. | A61C 1/084 433/213 |
| 2007/0281278 A1 * | 12/2007 | Jorneus | ................ | A61C 8/0001 433/173 |
| 2007/0281279 A1 * | 12/2007 | Chander | .............. | A61C 8/0001 433/173 |
| 2009/0104583 A1 * | 4/2009 | Yau | ...................... | A61C 8/0001 433/213 |

* cited by examiner

*Primary Examiner* — Ralph A Lewis

(74) *Attorney, Agent, or Firm* — McCarter & English, LLP

(57) ABSTRACT

Advantageous dental analogs for dental restorations and related methods of use are provided. The present disclosure provides improved analog members for use in fabricating dental implant-supported restorations, and related methods of use. More particularly, the present disclosure provides advantageous systems/methods for the design and use of protection analog members configured to protect cuff portions of coping members during the fabrication of dental restorations. The improved analog members include an added vertical rim or collar to contact and/or protect the cuff portion of coping members when an end of the analog member is screwed/mounted into place into an end of the coping member. This way, the resin added during fabrication will not contact/adhere to the cuff portion allowing a proper seating of the finished fixed implant-supported prosthesis. Use of the improved analog member also can eliminate scratches/damage to the cuff portion (e.g., during trimming and polishing).

20 Claims, 12 Drawing Sheets

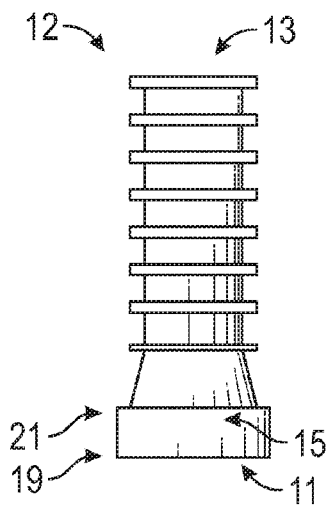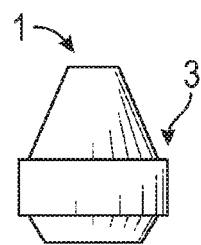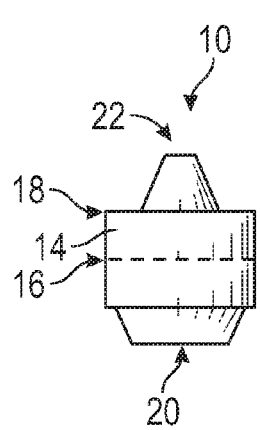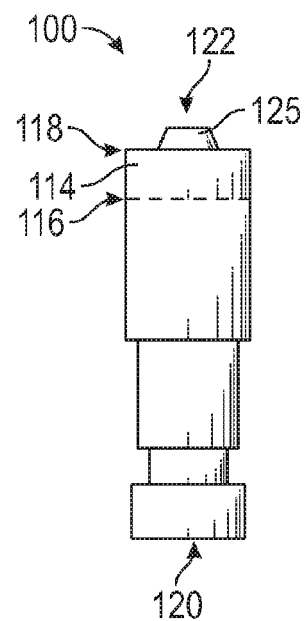
FIG. 1 (Prior Art)
FIG. 2 (Prior Art)
FIG. 3 (Prior Art)
FIG. 4
FIG. 5

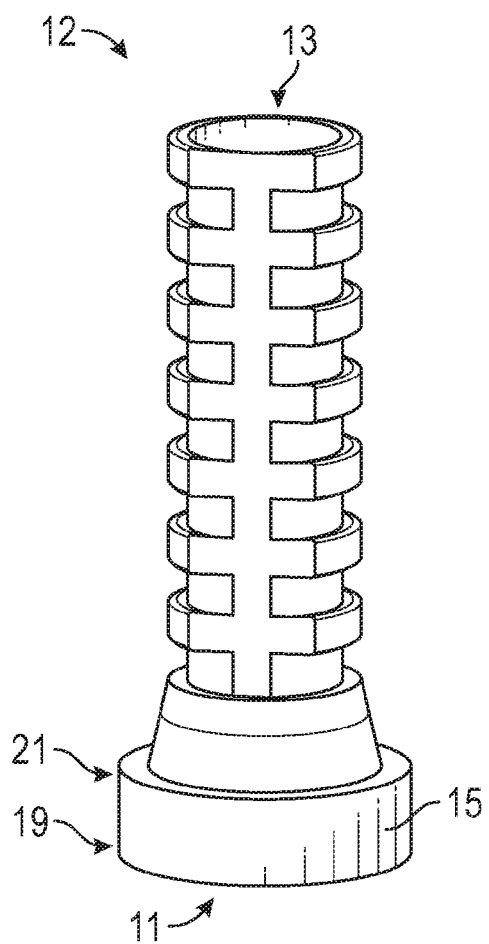 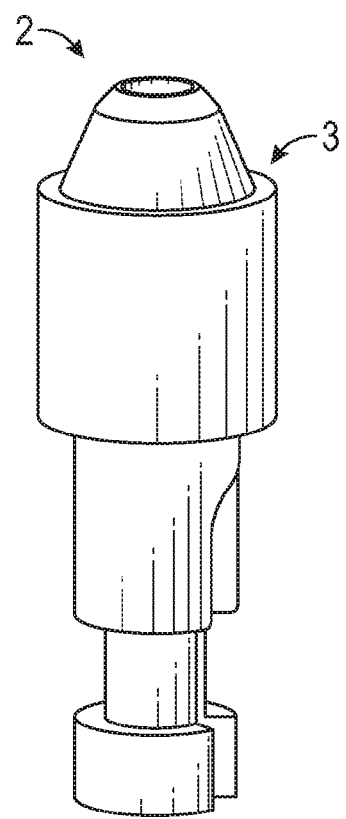
FIG. 10
(Prior Art)
FIG. 11
(Prior Art)

ANALOGS FOR DENTAL RESTORATIONS

CROSS-REFERENCE TO RELATED APPLICATIONS

This application claims the benefit of U.S. Provisional Application entitled "IMPROVED ANALOGS FOR USE IN MAKING DENTAL RESTORATIONS," which was filed on Jun. 28, 2016, and assigned Ser. No. 62/355,529, the contents of which are herein incorporated by reference in their entirety.

FIELD OF THE DISCLOSURE

The present disclosure relates to analog members for use in fabricating dental restorations and, more particularly to the design and use of protection analog members configured to protect cuff portions of coping members during the fabrication of dental implant-supported restorations.

BACKGROUND OF THE DISCLOSURE

Dental restorations are widely used in current dental care for replacing teeth that have been lost (e.g., to decay, cavities, gum disease, injury, etc.). Common examples of restorations include crowns for single tooth replacement, bridges to replace two or three teeth, and full or partial dentures for more extensive tooth replacement. In general, the restorations include several different components. The dental "implant" (also known as a fixture) is the component that is inserted into the jawbone mostly or completely below the gum line. An "abutment" is a connecting component that joins a visible component such as a crown, bridge or denture, to an implant. Abutments are generally made from titanium or other metals and may be either milled or cast. Abutment "analogs" (also known as replicas) can be identical in size and shape to part of particular abutments and are used in dental labs during fabrication of dental restorations. Some general information on the current state of the art in the field of dental restorations can be found at http://www.swdental-clinic.co.uk/documents/implantParts.pdf, the contents of which are herein incorporated by reference in their entirety.

Dental implants can be loaded either immediately after the implant has been surgically placed in a patient's jawbone or after some time (e.g., three months) of healing. Immediate loading for a full arch (e.g., missing all teeth in a given jaw) or full mouth is a popular procedure that can be accomplished using a minimum of four implants per jaw.

The dental bridge, typically made of a resin such as an acrylic resin, is attached to the implants by an intermediary machined component called the abutment. A machined metal coping (usually made of titanium) is then connected to the abutment using a prosthetic screw. The acrylic bridge is then fused to the machined metal coping using a resin such as an acrylic resin in the dental office or in the dental laboratory. The excess resin is then trimmed and polished. This way the polished acrylic bridge has four machined metal copings incorporated into it. The bridge is then seated and screwed down on to the abutments to provide the patient with a fixed (e.g., permanent/non-removable) set of teeth.

An interest exists for improved dental analogs and related components, and related methods of use. These and other inefficiencies and opportunities for improvement are addressed and/or overcome by the assemblies, systems and methods of the present disclosure.

SUMMARY OF THE DISCLOSURE

The present disclosure provides advantageous dental analogs for dental restorations, and improved methods/systems for using the same. The present disclosure provides improved analog members for use in fabricating dental implant-supported restorations, and related methods of use. More particularly, the present disclosure provides improved systems/methods for the design and use of protection analog members configured to protect the cuff portion of coping members during the fabrication of dental restorations.

Disclosed herein is a solution to the problem of having excess resin on a coping member (e.g., machined metal coping member). Such excess resin should be removed before the coping member is used in the fabrication of a bridge or denture. For example, most coping members (e.g., machined metal copings) have a cuff portion (e.g., shiny metal cuff portion), which should be free of resin so that the final bridge fits properly over the abutments without gaps or without undue stresses on the acrylic bridge. Any marginal gaps or undue stresses on the acrylic bridge may result in fracture of the bridge and failure of the implants and related components (especially in immediate loading situations during the healing stage). Excess resin over the metal cuff portion of the machined metal copings can impede insertion (seating) of the acrylic bridge itself resulting in repair and remake of the entire bridge.

Disclosed herein is a significant improvement over existing products variously called "protection analogs," "polishing caps" or "abutment analogs." These products are used to attempt to protect the cuff portion (e.g., metal cuff portion) of coping members during the fabrication, polishing and trimming steps that may be carried out in a dental lab or office in order to produce restorations such as bridges and dentures.

The improved analog members disclosed herein advantageously include an added vertical rim or collar to contact and/or protect the cuff portion (e.g., shiny metal cuff portion) of the coping member when an end (e.g., convex end) of the analog member is screwed or mounted into place into an end (e.g., concave end) of the coping member. This way, the resin (e.g., acrylic resin) added during the fabrication process will not contact and adhere to the cuff portion (metal cuff portion). Use of the improved analog member also can eliminate scratches or damage to the cuff portion (e.g., during trimming and polishing). Otherwise, scratches or damage to the cuff portion (metal cuff portion) can readily become a trap for bacteria and plaque and the like, resulting in soft tissue inflammation and possible bone loss around the implants.

The present disclosure provides for a dental analog member including a body that extends from a first end to a second end, the second end including a mounting member configured to mount to a mounting end of a coping member, the mounting end of the coping member including a cuff portion that extends from a first end to a second end; an extending collar portion of the body that extends from a first end to a second end, the extending collar portion positioned proximal to the mounting member of the second end of the body; wherein after the mounting member of the second end of the body is mounted to the mounting end of the coping member, the extending collar portion houses and covers the cuff portion of the coping member.

The present disclosure also provides for a dental analog member wherein the mounting member of the second end of the body is a convex mounting member; and wherein the mounting end of the coping member includes a concave mounting end. The present disclosure also provides for a dental analog member wherein the first end of the body includes a dental abutment feature or dimension.

The present disclosure also provides for a dental analog member wherein the extending collar portion substantially matches the dimensions of the cuff portion of the coping member. The present disclosure also provides for a dental analog member wherein after the extending collar portion houses and covers the cuff portion of the coping member, the extending collar portion prevents resin added during a fabrication process from adhering to the cuff portion of the coping member.

The present disclosure also provides for a dental analog member wherein the first end of the extending collar portion is positioned proximal to an interior abutment surface of the body, the interior abutment surface configured to abut against the first end of the cuff portion when the mounting member of the second end of the body is mounted to the mounting end of the coping member.

The present disclosure also provides for a dental analog member wherein the extending collar portion defines a protective receiving cavity configured to house the cuff portion of the coping member. The present disclosure also provides for a dental analog member wherein the protective receiving cavity is defined between the extending collar portion and the mounting member of the second end of the body. The present disclosure also provides for a dental analog member wherein the protective receiving cavity is configured to house or contain the cuff portion between the extending collar portion and the mounting member, and is configured to house or contain the cuff portion between the first and second ends of the extending collar portion.

The present disclosure also provides for a dental analog member wherein the extending collar portion is removable or replaceable relative to the body.

The present disclosure also provides for a method for utilizing a dental analog member including providing a body that extends from a first end to a second end, the second end including a mounting member, the body having an extending collar portion that extends from a first end to a second end, the extending collar portion positioned proximal to the mounting member of the second end of the body; providing a coping member having a mounting end, the mounting end of the coping member including a cuff portion that extends from a first end to a second end; mounting the mounting member of the second end of the body to the mounting end of the coping member; wherein after the mounting member of the second end of the body is mounted to the mounting end of the coping member, the extending collar portion houses and covers the cuff portion of the coping member.

The present disclosure also provides for a method for utilizing a dental analog member wherein the mounting member of the second end of the body is a convex mounting member; and wherein the mounting end of the coping member includes a concave mounting end. The present disclosure also provides for a method for utilizing a dental analog member wherein the first end of the body includes a dental abutment feature or dimension.

The present disclosure also provides for a method for utilizing a dental analog member wherein the extending collar portion substantially matches the dimensions of the cuff portion of the coping member. The present disclosure also provides for a method for utilizing a dental analog member wherein after the extending collar portion houses and covers the cuff portion of the coping member, the extending collar portion prevents resin added during a fabrication process from adhering to the cuff portion of the coping member.

The present disclosure also provides for a method for utilizing a dental analog member wherein the first end of the extending collar portion is positioned proximal to an interior abutment surface of the body, the interior abutment surface configured to abut against the first end of the cuff portion when the mounting member of the second end of the body is mounted to the mounting end of the coping member.

The present disclosure also provides for a method for utilizing a dental analog member wherein the extending collar portion defines a protective receiving cavity configured to house the cuff portion of the coping member; and wherein the protective receiving cavity is defined between the extending collar portion and the mounting member of the second end of the body. The present disclosure also provides for a method for utilizing a dental analog member wherein the protective receiving cavity is configured to house or contain the cuff portion between the extending collar portion and the mounting member, and is configured to house or contain the cuff portion between the first and second ends of the extending collar portion. The present disclosure also provides for a method for utilizing a dental analog member wherein the extending collar portion is removable or replaceable relative to the body.

The present disclosure also provides for a dental analog member including a body that extends from a first end to a second end, the second end including a convex mounting member configured to mount to a concave mounting end of a coping member, the concave mounting end of the coping member including a cuff portion that extends from a first end to a second end; an extending collar portion of the body that extends from a first end to a second end, the extending collar portion positioned proximal to the convex mounting member of the second end of the body; wherein after the convex mounting member of the second end of the body is mounted to the concave mounting end of the coping member, the extending collar portion houses and covers the cuff portion of the coping member; wherein after the extending collar portion houses and covers the cuff portion of the coping member, the extending collar portion prevents resin added during a fabrication process from adhering to the cuff portion of the coping member; wherein the first end of the extending collar portion is positioned proximal to an interior abutment surface of the body, the interior abutment surface configured to abut against the first end of the cuff portion when the convex mounting member of the second end of the body is mounted to the concave mounting end of the coping member; wherein the extending collar portion defines a protective receiving cavity configured to house the cuff portion of the coping member; wherein the protective receiving cavity is defined between the extending collar portion and the convex mounting member of the second end of the body; and wherein the protective receiving cavity is configured to house or contain the cuff portion between the extending collar portion and the convex mounting member, and is configured to house or contain the cuff portion between the first and second ends of the extending collar portion.

Any combination or permutation of embodiments is envisioned. Additional advantageous features, functions and applications of the disclosed systems, methods and assemblies of the present disclosure will be apparent from the description which follows, particularly when read in conjunction with the appended figures. All references and documents listed in this disclosure are hereby incorporated by reference in their entireties.

BRIEF DESCRIPTION OF THE DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various features, steps and combinations of features/steps described below and illustrated in the figures can be arranged and organized differently to result in embodiments which are still within the scope of the present disclosure. To assist those of ordinary skill in the art in making and using the disclosed assemblies, systems and methods, reference is made to the appended figures, wherein:

FIG. 1 is a side view of a coping member;

FIG. 2 is a side view of a protection analog member;

FIG. 3 is a side view of a conventional analog member;

FIG. 4 is a side view of an exemplary protection analog member according to the present disclosure;

FIG. 5 is a side view of an exemplary analog member according to the present disclosure;

FIG. 10 is a side view of a commercially available coping member that is used to connect a patient's acrylic resin bridge to the patient's dental implants in the mouth; the coping member includes a cuff portion at the base of the coping member that should be left intact and undamaged during the process of connecting the coping member to the denture and making the fixed implant bridge;

FIG. 11 is a side view of a conventional analog member that can be used to connect to the coping member to attempt to prevent excessive acrylic resin from getting inside the coping member and also can assist during finishing and polishing;

DETAILED DESCRIPTION OF DISCLOSURE

Figure 6:
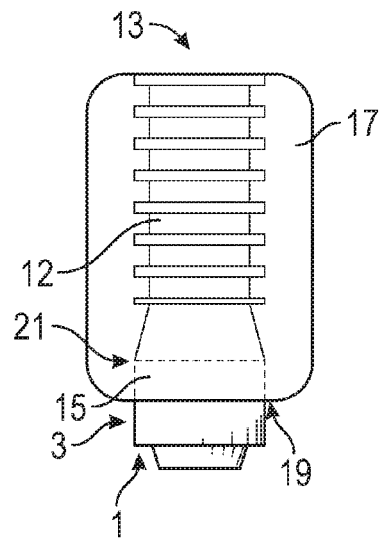
FIG. 6 is a side view of a protection analog member mounted to a coping member.

The exemplary embodiments disclosed herein are illustrative of advantageous analog members for dental restorations, and systems of the present disclosure and methods/techniques thereof. It should be understood, however, that the disclosed embodiments are merely exemplary of the present disclosure, which may be embodied in various forms. Therefore, details disclosed herein with reference to exemplary members/fabrication methods and associated processes/techniques of assembly and use are not to be interpreted as limiting, but merely as the basis for teaching one skilled in the art how to make and use the advantageous members/systems and/or alternative members of the present disclosure.

The present disclosure provides dental analog members for dental restorations, and improved methods/systems for using the same. The present disclosure provides advantageous analog members for use in fabricating dental implant-supported restorations, and related methods of use. More particularly, the present disclosure provides advantageous systems/methods for the design and use of protection analog members configured to protect cuff portions of coping members during the fabrication of dental restorations (e.g., for full arch or partial arch fixed prostheses).

In exemplary embodiments and as noted, the present disclosure provides for a solution to the problem of having excess resin on a coping member, as excess resin should be removed before the coping member is used in the fabrication of a dental restoration. Most coping members have a cuff portion, which generally must be free of resin so that the final bridge fits properly over the abutments.

In exemplary embodiments, the present disclosure provides for a significant improvement over conventional analog members (e.g., protection analogs, polishing caps, abutment analogs, etc.). The improved analog members disclosed herein advantageously include an added vertical rim or collar to contact and/or protect the cuff portion (e.g., shiny metal cuff portion) of the coping member when an end (e.g., convex end) of the analog member is screwed or mounted into place into an end (e.g., concave end) of the coping member. This way, the resin (e.g., acrylic resin) added during the fabrication process will not contact and adhere to the cuff portion. Use of the improved analog member also can substantially eliminate scratches or damage to the cuff portion (e.g., during trimming and polishing). Otherwise, scratches or damage to the cuff portion can readily become a trap for bacteria and plaque and the like.

Current practice provides that several approaches have been used to attempt to protect coping members (e.g., metal implant copings) from resins (e.g., acrylic resin) and the potential damage that results from removing excess resin. Some known approaches involve lubricating the metal cuff portion with petrolatum jelly or with Teflon tape to attempt to prevent adhesion of the acrylic resin, and then carefully scraping away inadvertent acrylic resin. A disadvantage of this approach is that it is very hard to eliminate the resin from adhering to the metal cuff portion and the cuff portion may still get scratched during trimming and polishing.

A further known approach is ignoring the metal cuff portion and simply trimming away acrylic resin that adheres to it at a later stage. Some disadvantages of this approach is that it is not good clinical practice nor is it in the best interest of the patient because the scratches or damage to the metal cuff becomes a bacteria and plaque trap resulting in soft tissue inflammation and possible bone loss around the implants.

Another conventional approach to the problem is to not use any abutments at all and, alternatively, to connect the bridge directly to the implants. The metal copings that connect directly to implants do not have the metal cuff that is of interest here. A disadvantage to this approach is that very few patients actually have the bone volume where implants can be placed in positions that lend themselves to direct connection. Additionally, direct connection to implants has a plethora of additional practical disadvantages such as difficulty in regular repairs and maintenance, difficulty in confirming seating of the prosthesis, difficulty in assessment of passive fit, etc.

In exemplary embodiments of the present disclosure, a vertical rim or collar is advantageously provided on an analog member, with the rim/collar closely matching the dimensions of the cuff portion of the coping member, thereby addressing multiple problems. For example, the disclosed analog member substantially eliminates the possibility for resin (e.g., acrylic resin) to adhere to the cuff portion, which makes trimming and polishing of the acrylic bridge simple, easy and quick.

The disclosed and improved analog member ensures that the acrylic bridge will be free of damage or scratches and will seat passively without gaps between the coping member and the abutment. This can prevent fracture of the bridge and can prevent failure of the dental implants and components (especially in immediate loading situations). The disclosed analog member ensures that the acrylic bridge will be substantially free of damage or scratches and can ensure that the cuff portion (e.g., metal cuff portion) remains smooth and does not become a bacteria and/or plaque trap, thereby substantially eliminating soft tissue inflammation and possible bone loss around the implants.

Referring now to the drawings, like parts are marked throughout the specification and drawings with the same reference numerals, respectively. Drawing figures are not necessarily to scale and in certain views, parts may have been exaggerated for purposes of clarity.

FIGS. 1 and 10 depict a conventional coping member 12 for use in the fabrication of a dental restoration or the like. In general, coping member 12 extends from a first end 11 to a second end 13, and typically includes a cuff portion 15 proximal to first end 11. As discussed further below, cuff portion 15 of coping member 12 should be substantially free of resin 17 so that the final bridge fits properly over the abutments. The cuff portion 15 of coping member 12 extends from a first end 19 to a second end 21.

An exemplary dental protection analog member 10 of the present disclosure is depicted in FIG. 4, the analog member 10 having a body extending from a first end 20 to a second end 22. An exemplary dental analog member 100 of the present disclosure is depicted in FIG. 5, the analog member 100 having a body extending from a first end 120 to a second end 122.

In general, dental analog members 10, 100 can be substantially identical in size and shape to at least part of particular dental abutments and can be used in dental labs during fabrication of dental restorations depending upon the choice of the operator. At least portions of first end 20, 120 and/or second end 22, 122 of analog member 10, 100 typically include dental abutment features/dimensions and/or mounting features/members or the like.

The present disclosure provides for a solution to the problem of having excess resin 17 on a coping member 12, as excess resin 17 should be removed before the coping member 12 is used in the fabrication of a dental restoration. Many coping members 12 have cuff portion 15, which should be free of resin 17 so that the final bridge fits properly over the abutments.

Figure 7:
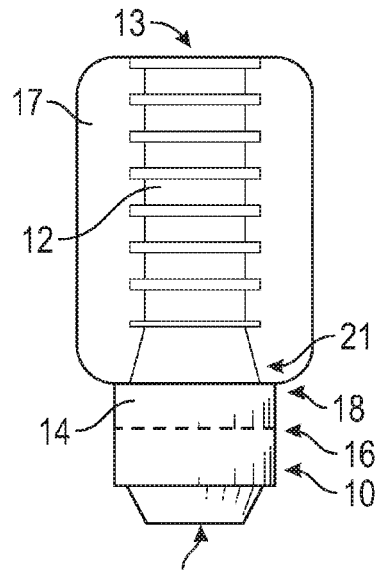
FIG. 7 is a side view of the exemplary protection analog member of FIG. 4 mounted to a coping member.
Figure 9:
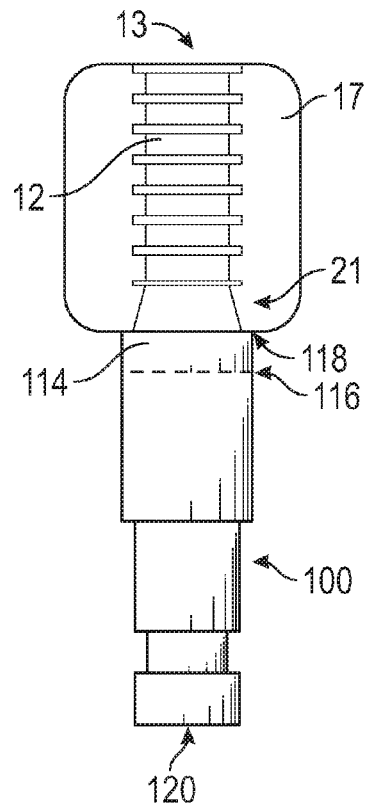
FIG. 9 is a side view of the exemplary analog member of FIG. 5 mounted to a coping member.
Figure 12:
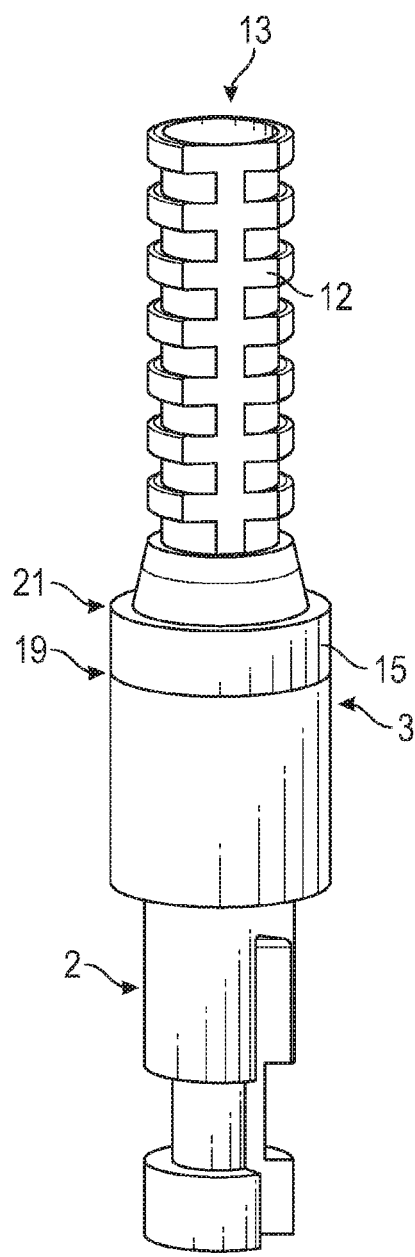
FIG. 12 is a side view showing how the coping member of FIG. 10 (upper) and the analog member of FIG. 11 (lower) connect with each other; this is a "flat to flat" connection and the metal cuff portion of the coping member is exposed (e.g., it is not protected)
Figure 13:
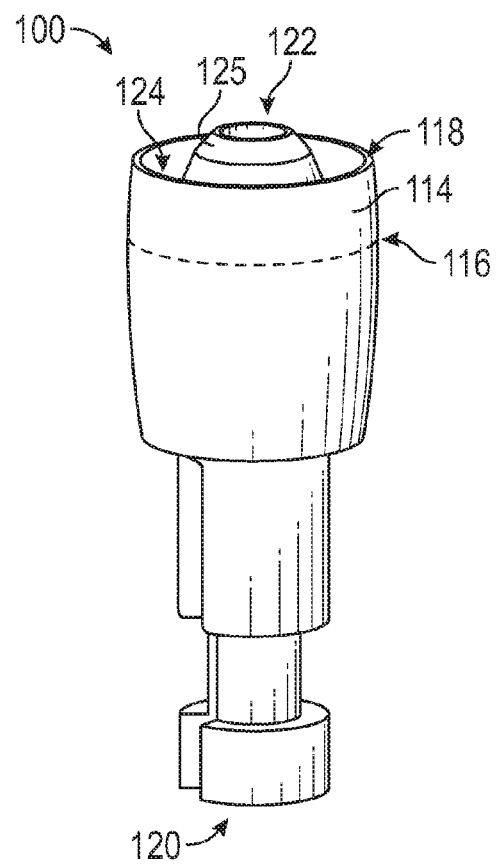
FIG. 13 is a side view of an exemplary analog member according to the present disclosure; the extension "rim" or extending collar portion of the analog member has been designed to substantially match and/or cover the dimensions of the coping member (e.g., cuff portion) that should be protected.
Figure 14:
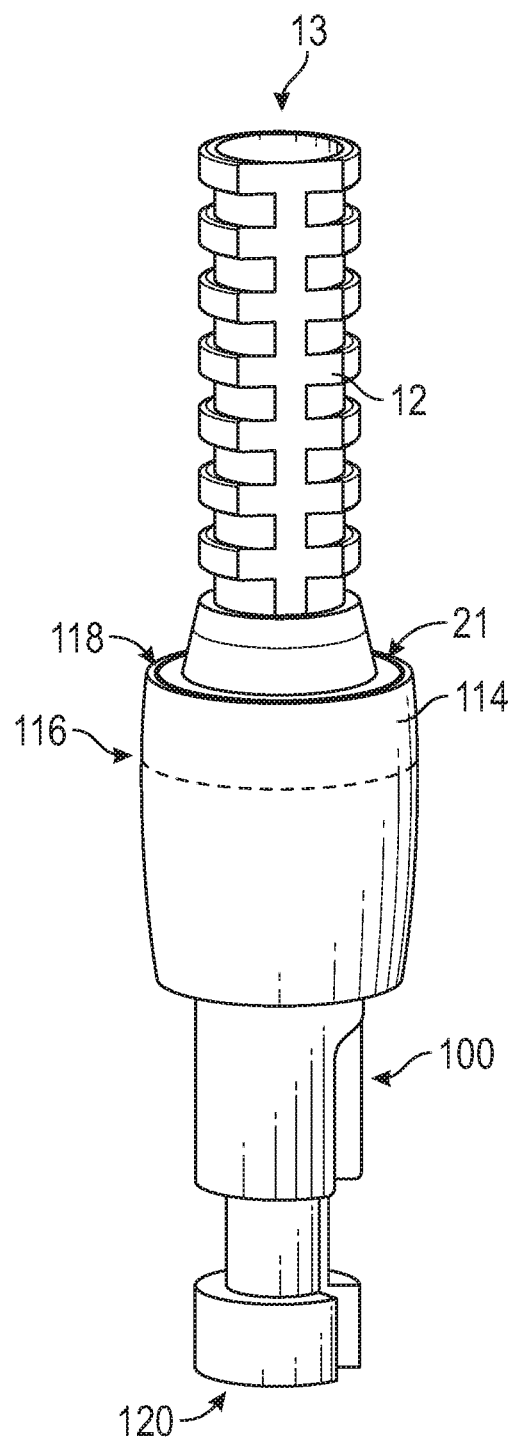
FIG. 14 is a side view showing how the coping member of FIG. 10 (upper) and the exemplary analog member of FIG. 13 (lower) connect with each other; this is not a flat to flat connection, and the cuff portion of the coping member is protected due to the extension rim or extending collar portion of the analog member that was designed to substantially match and/or cover the dimensions of the coping member (e.g., cuff portion) that should be protected.

The present disclosure provides for a significant improvement over conventional analog members 1, 2 (e.g., protection analogs 1, polishing caps 1, abutment analogs 2, etc.—FIGS. 2 and 3). The improved analog members 10, 100 disclosed herein advantageously include an extending collar portion 14, 114 that extends from a first end 16 (or 116) to a second end 18 (or 118), the extending collar portion 14, 114 configured to surround, house, contact and/or protect the cuff portion 15 (e.g., shiny metal cuff portion 15) of the coping member 15 when a second end 22, 122 (e.g., convex end 22, 122) of the analog member 10, 100 is screwed or mounted into place into the first end 11 (e.g., concave end 11) of the coping member 12. This way, the resin 17 (e.g., acrylic resin 17) added during the fabrication process will not contact and adhere to the cuff portion 15 (FIGS. 7 and 9). Use of the improved analog members 10, 100 can substantially eliminate scratches or damage to the cuff portion 15 (e.g., during trimming and polishing). Otherwise, scratches or damage to the cuff portion 15 can readily become a trap for bacteria and plaque and the like.

Figure 8:
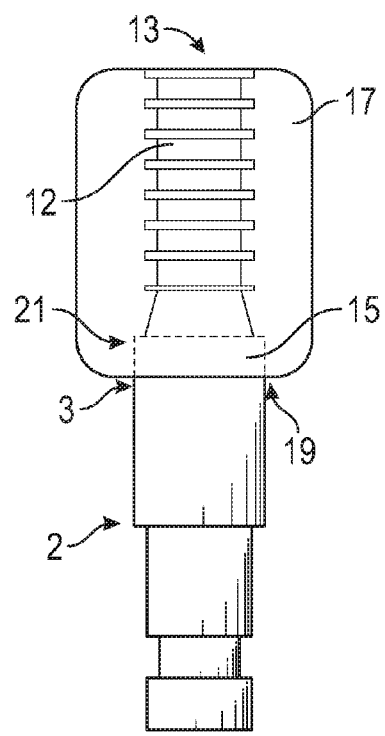
FIG. 8 is a side view of a conventional analog member mounted to a coping member.

For example, current practice provides that conventional analog members 1, 2 may be mounted to first end 11 of coping member 12, with a connecting region 3 of members 1, 2 positioned adjacent to first end 19 of cuff portion 15 (FIGS. 6 and 8). Such "flat-to-flat" connection between analog members 1, 2 with coping member 12 thereby exposes cuff portion 15 to excess resin 17, as depicted in FIGS. 6 and 8.

A disadvantage of such approach is that the resin 17 typically will adhere to the metal cuff portion 15 (FIGS. 6 and 8), and the cuff portion 15 generally will get scratched during trimming and polishing. This approach is not in the best interest of the patient because the scratches or damage to the metal cuff 15 becomes a bacteria and plaque trap resulting in soft tissue inflammation and possible bone loss around the implants.

In exemplary embodiments of the present disclosure, analog member 10, 100 includes extending collar portion 14, 114, with the extending collar portion 14, 114 closely or substantially matching the dimensions of the cuff portion 15 of the coping member 12, thereby addressing multiple problems. For example, the disclosed analog member 10, 100 substantially eliminates or prevents the possibility for resin 17 (e.g., acrylic resin 17) to adhere to the cuff portion 17 (see FIGS. 7 and 9), which makes trimming and polishing of the acrylic bridge simple, easy and quick.

More particularly and as noted, analog members 10, 100 include extending collar portion 14, 114 that extends from a first end 16, 116 to a second end 18, 118), the extending collar portion 14, 114 configured to surround, house, contact and/or protect the cuff portion 15 when a second end 22, 122 of the analog member 10, 100 is mounted into place into the first end 11 of the coping member 12. This way, the resin 17 added during the fabrication process will not contact and adhere to the cuff portion 15 (FIGS. 7 and 9).

Figure 15:
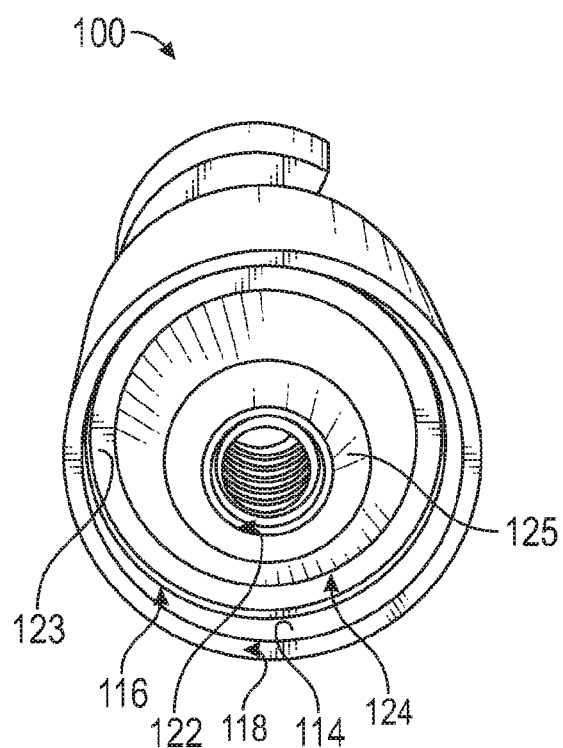
FIG. 15 is an end view (internal) of the exemplary analog member of FIG. 13; this close-up view of an internal aspect of an end of an analog member with cuff protector or extending collar portion that connects to a coping member shows the projected rim or extending collar portion that emerges/extends with a dimension to cover and protect the coping member (e.g., cuff portion or extending collar portion)
Figure 16:
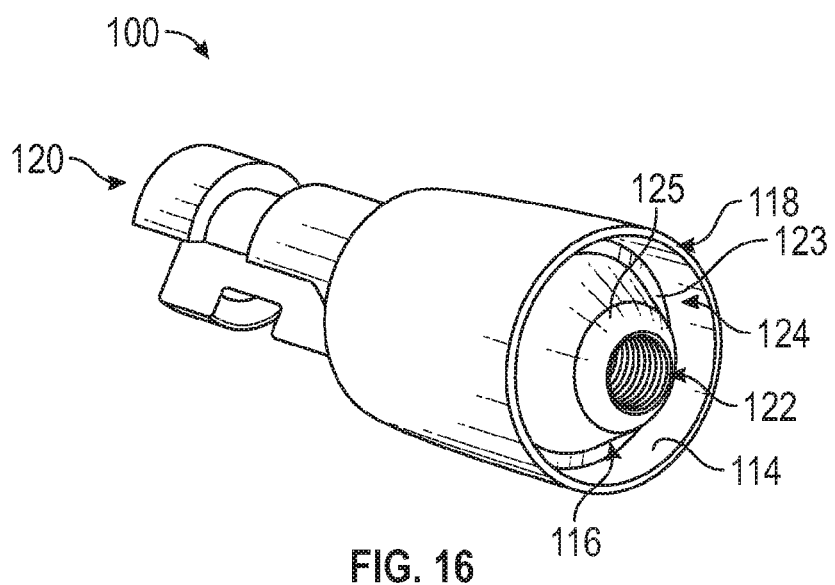
FIG. 16 is a side perspective view of the exemplary analog member of FIG. 13 that shows the emergence and extension of the cuff protector or extending collar portion that has an extending projection or portion configured to protect the coping member (e.g., cuff portion or extending collar portion)

As shown in FIGS. 15 and 16, first end 116 of exemplary extending collar portion 114 is positioned proximal to an interior abutment wall/surface 123 of analog member 100, the interior abutment wall/surface 123 configured and dimensioned to engage or abut against the first end 19 of the cuff portion 15 when the second end 122 of analog member 100 is mounted to first end 11 of coping member 12, thereby housing, covering and/or protecting cuff portion 15 with the advantageous extending collar portion 114.

In certain embodiments, extending collar portion 114 defines a protective receiving cavity 124 for cuff portion 15, the receiving cavity 124 defined between the extending collar portion 114 and a mounting member 125 (e.g., convex protruding mounting member 125) of second end 122 of analog member 100. In general, exemplary receiving cavity 124 is configured and dimensioned to house and/or contain the cuff portion 15 between the extending collar portion 114 (exterior to portion 15) and the mounting member 125 (interior to portion 15), and is configured and dimensioned to house and/or contain the cuff portion 15 between the first and second ends 116, 118 of extending collar portion 114.

In some embodiments, it is noted that extending collar portion 14, 114 of analog member 10, 100 may be removable, detachable and/or replaceable relative to the body of analog member 10, 100.

As noted, the disclosed analog member 10, 100 substantially eliminates the possibility for resin 17 (e.g., acrylic resin 17) to adhere to the cuff portion 17 (see FIGS. 7 and 9), which makes trimming and polishing of the acrylic bridge simple, easy and quick. As such, the disclosed and improved analog member 10, 100 ensures that the acrylic bridge will be free of damage or scratches and will seat passively without gaps between the coping member 12 and the abutment. This can prevent fracture of the bridge and can prevent failure of the dental implants and components (especially in immediate loading situations). The disclosed analog member 10, 100 ensures that the acrylic bridge will be substantially free of damage or scratches and can ensure that the cuff portion 15 (e.g., metal cuff portion 15) remains smooth and does not become a bacteria and/or plaque trap, thereby substantially eliminating soft tissue inflammation and possible bone loss around the resultant implants.

Figure 17:
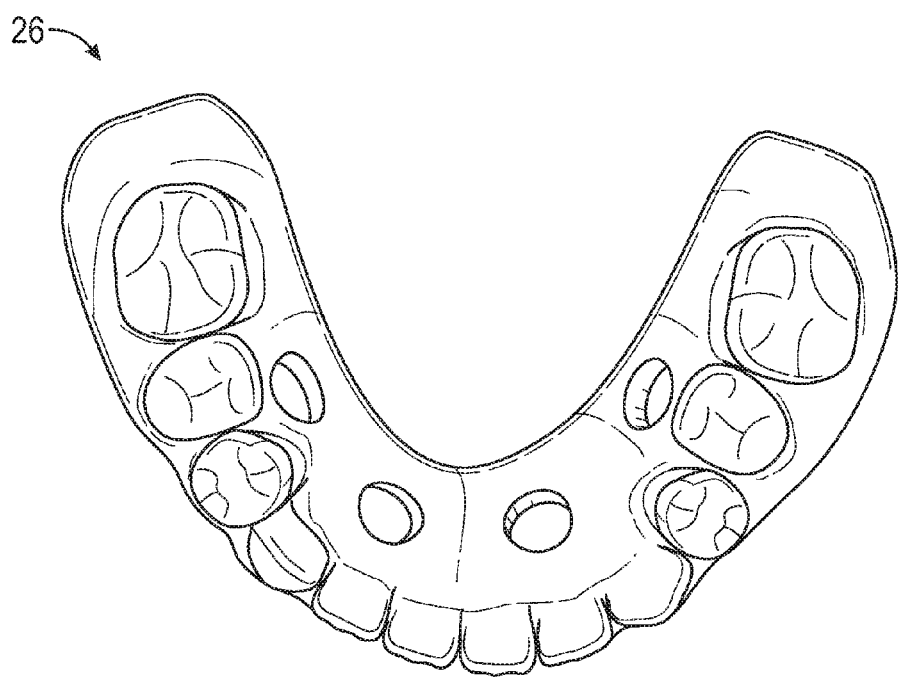
FIG. 17 is a top view of a patient's lower denture ready to be converted to a fixed implant bridge; note the four holes.

FIG. 17 is a top view of a patient's lower denture 26 ready to be converted to a fixed implant bridge.

Figure 18:
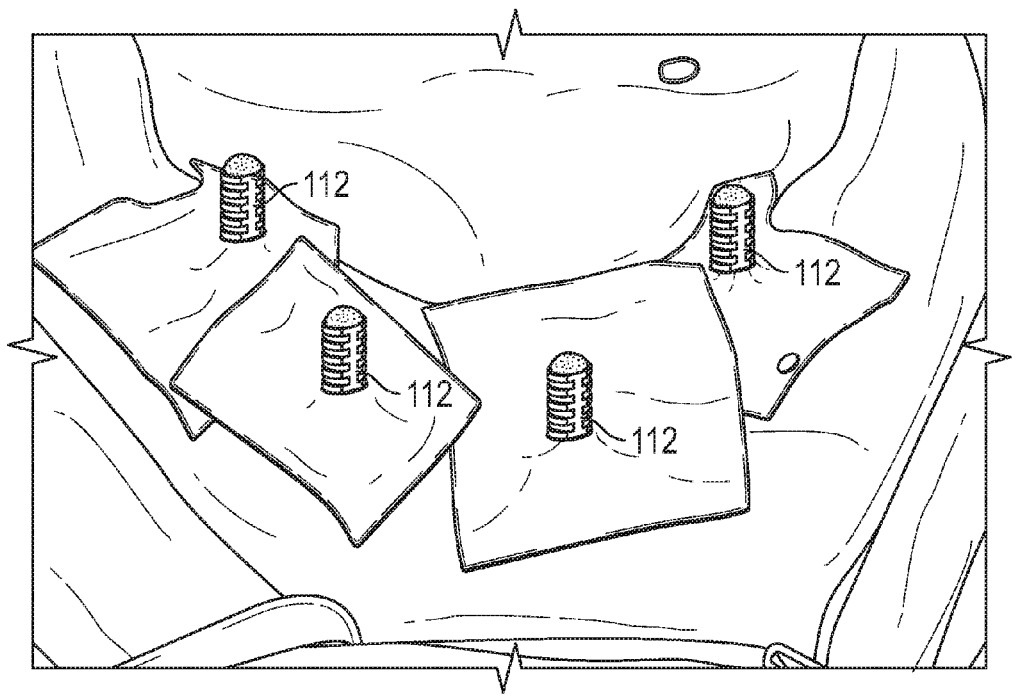
FIG. 18 depicts temporary coping members (FIG. 10) in the mouth with rubber dams used to prevent locking of resin material.
Figure 19:
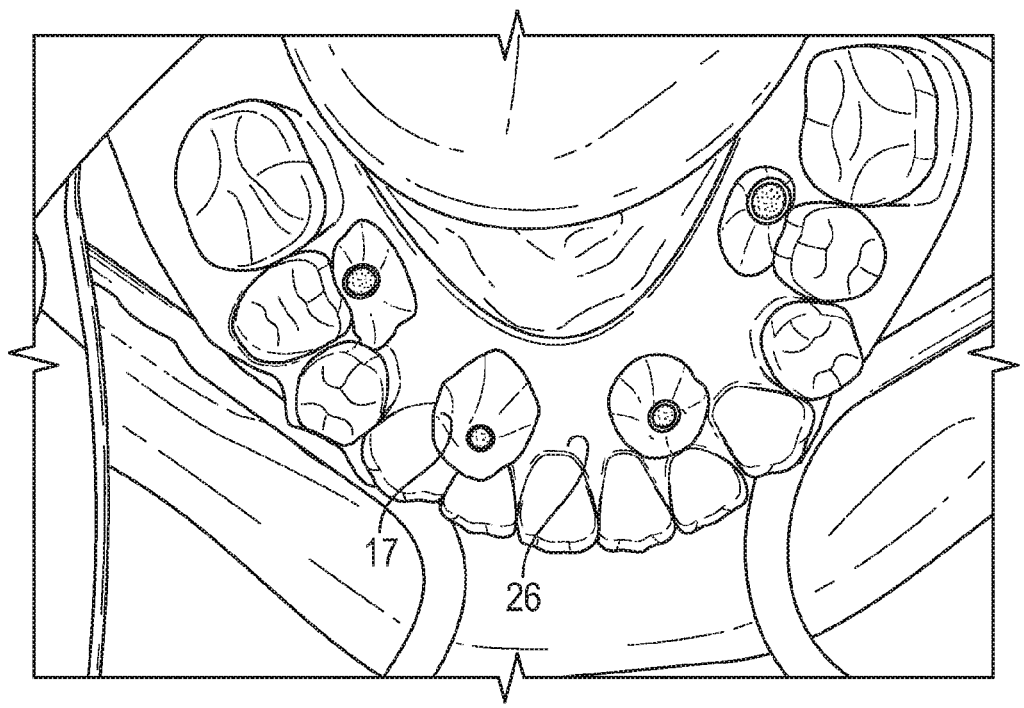
FIG. 19 depicts a denture being connected to the implants using resin.
Figure 20:
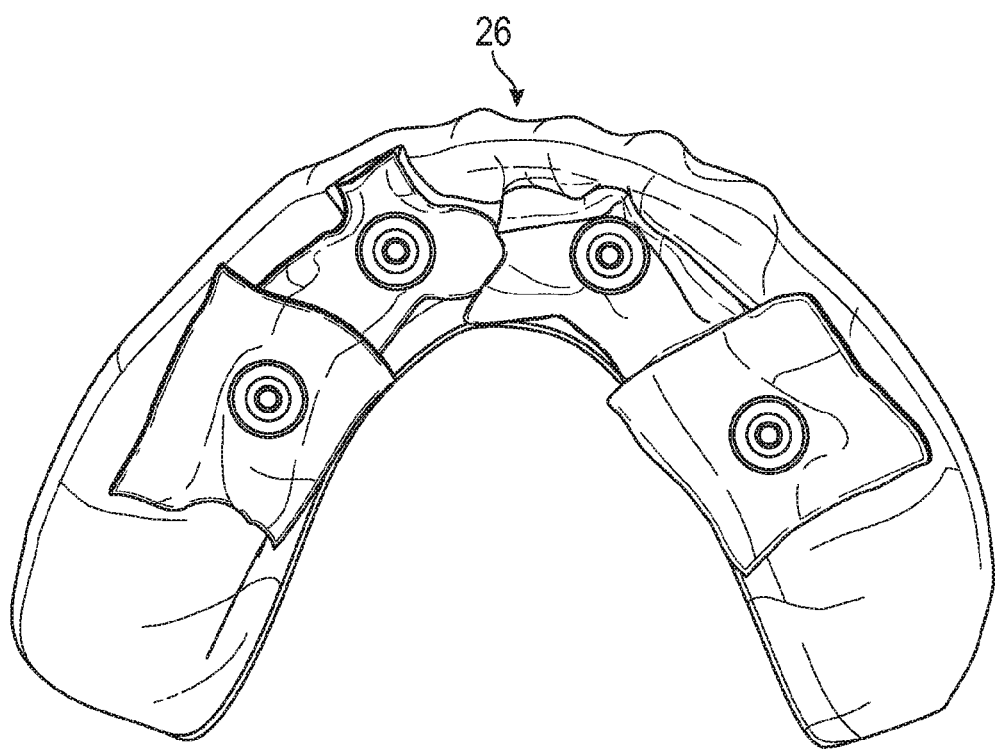
FIG. 20 depicts the intaglio surface of the denture immediately after removal from the mouth; the denture is ready to be converted to a fixed implant bridge.

FIG. 18 depicts temporary coping members 112 in the mouth with rubber dams used to prevent locking of resin material. FIG. 19 depicts a denture 26 being connected to the implants using resin 17. FIG. 20 depicts the intaglio surface of the denture 26 immediately after removal from the mouth. The denture 26 is now ready to be converted to a fixed implant bridge.

Figure 21:
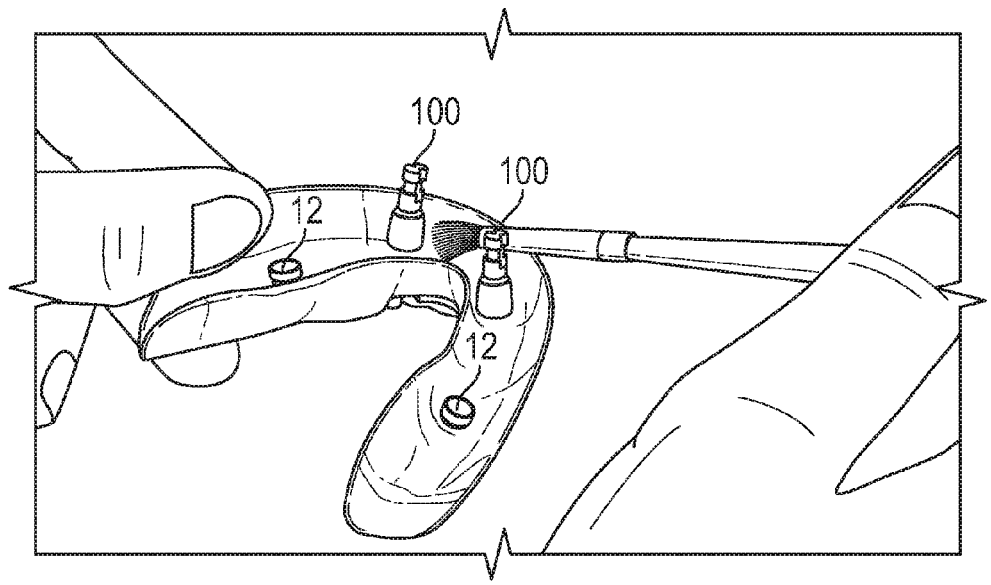
FIG. 21 depicts exemplary analog members (FIGS. 13 and 14) of the present disclosure after securement into two front coping members and resin can be added for the conversion process.
Figure 22:
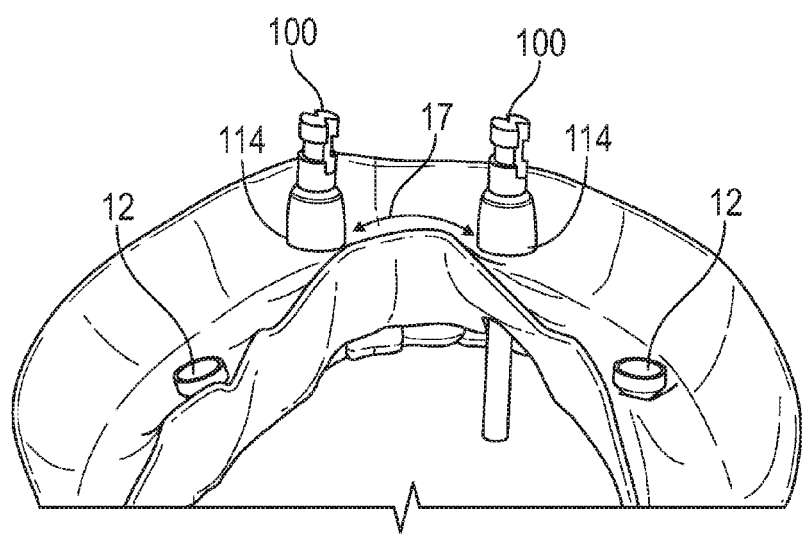
FIG. 22 depicts two exemplary analog members (FIGS. 13 and 14) protecting a respective cuff portion of a coping member while resin is setting.

FIG. 21 depicts exemplary analog members 100 of the present disclosure after securement into two front coping members 12 and resin can be added for the conversion process. FIG. 22 depicts two exemplary analog members 100 protecting a respective cuff portion of a coping member while resin 17 is setting.

Figure 23:
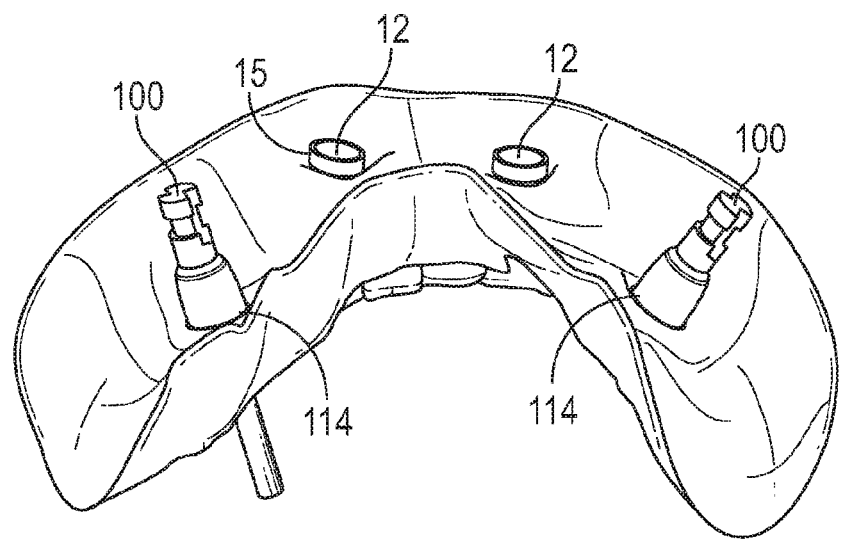
FIG. 23 depicts that after resin is set in the front region, two exemplary analog members can then screwed into two posterior (back) coping members (FIGS. 13 and 14) and resin can be added for the conversion process.

FIG. 23 depicts that after resin is set in the front region, two exemplary analog members 100 can then screwed into two posterior (back) coping members 12 and resin 17 can be added for the conversion process.

Figure 24:
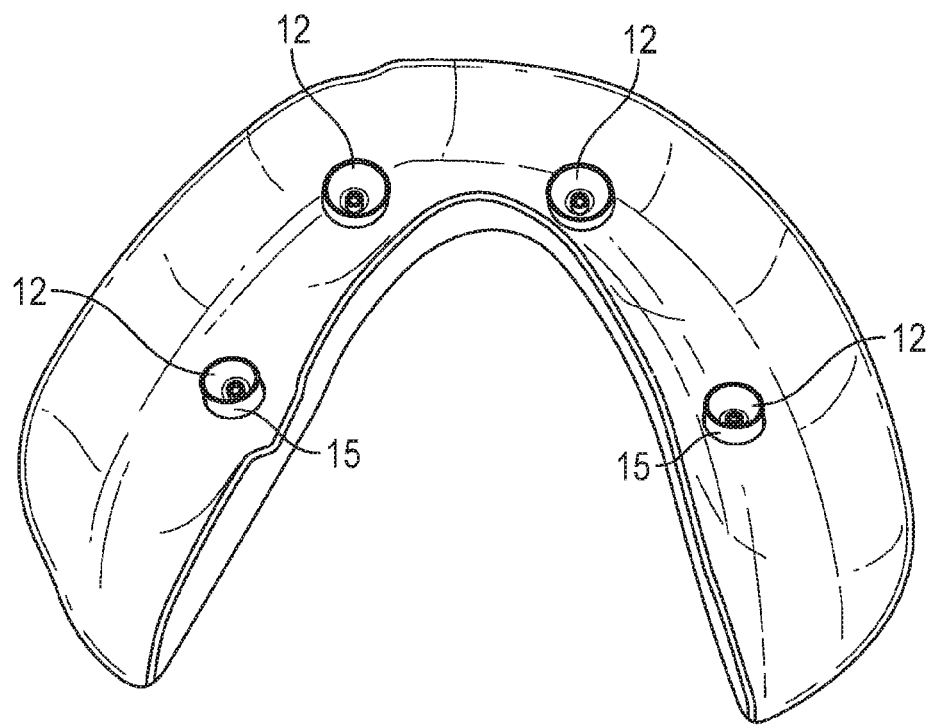
FIG. 24 shows an image of the denture after removal of the exemplary analog members, with the cuff portions on all four coping being substantially free of resin thereby indicating that the analog members with cuff protectors were effective.

FIG. 24 shows an image of the denture 26 after removal of the exemplary analog members 100, with the cuff portions 15 on all four coping members 12 being substantially free of resin 17 thereby indicating that the analog members 100 with cuff protectors or extending collar portions 114 were effective.

Figure 25:
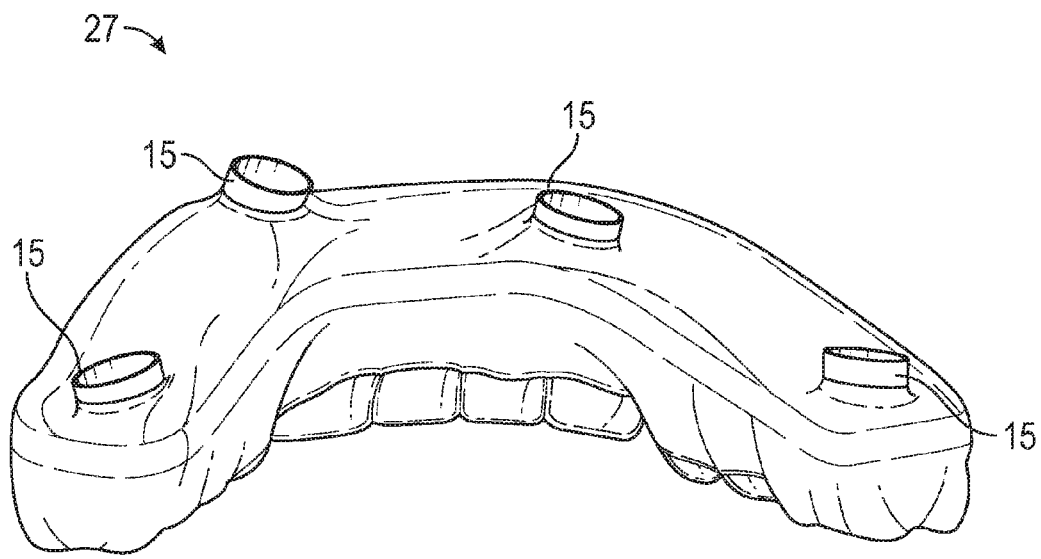
FIG. 25 shows the tissue surface of the fixed implant bridge after trimming and finishing using the exemplary analog members; note the absence of resin on the cuff portions, again showing the effectiveness of the cuff protectors of the exemplary analog members.

FIG. 25 shows the tissue surface of the fixed implant bridge 27 after trimming and finishing using the exemplary analog members 100. The absence of resin 17 on the cuff portions 15 is noted, again showing the effectiveness of the cuff protectors or extending collar portions 114 of the exemplary analog members 100.

Figure 26:
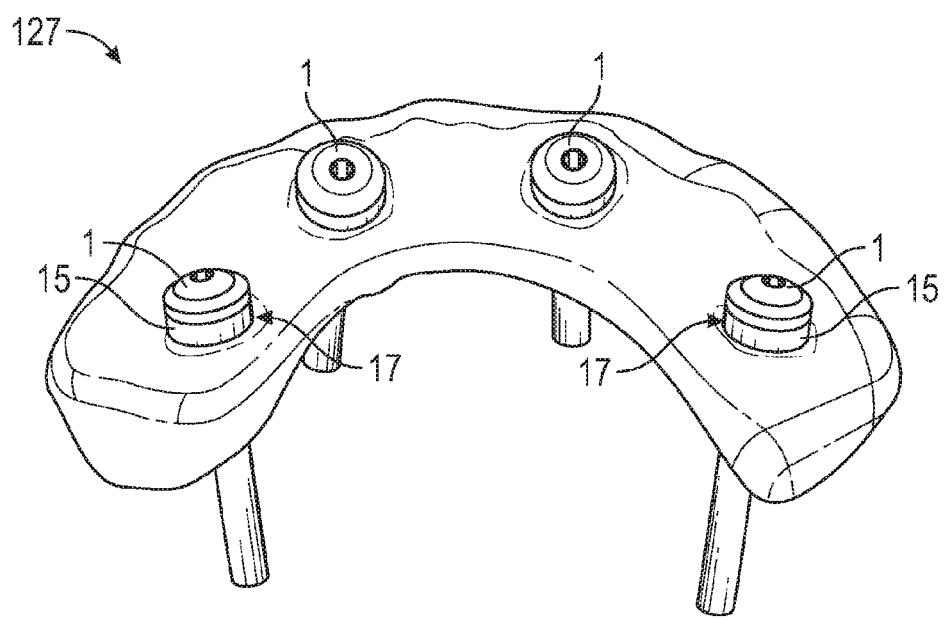
FIG. 26 shows a contrasting image from another patient showing use of a commercially available protection analog over the coping members during conversion to a fixed implant bridge; these protection analogs do not adequately protect the cuff portions and some resin material can be seen adhering to the cuff portions.

FIG. 26 shows a contrasting image from another patient showing use of a commercially available protection analog 1 over the coping members 12 during conversion to a fixed implant bridge 127. These protection analogs 1 do not adequately protect the cuff portions 15 and resin material 17 can be seen adhering to the cuff portions 15.

Figure 27:
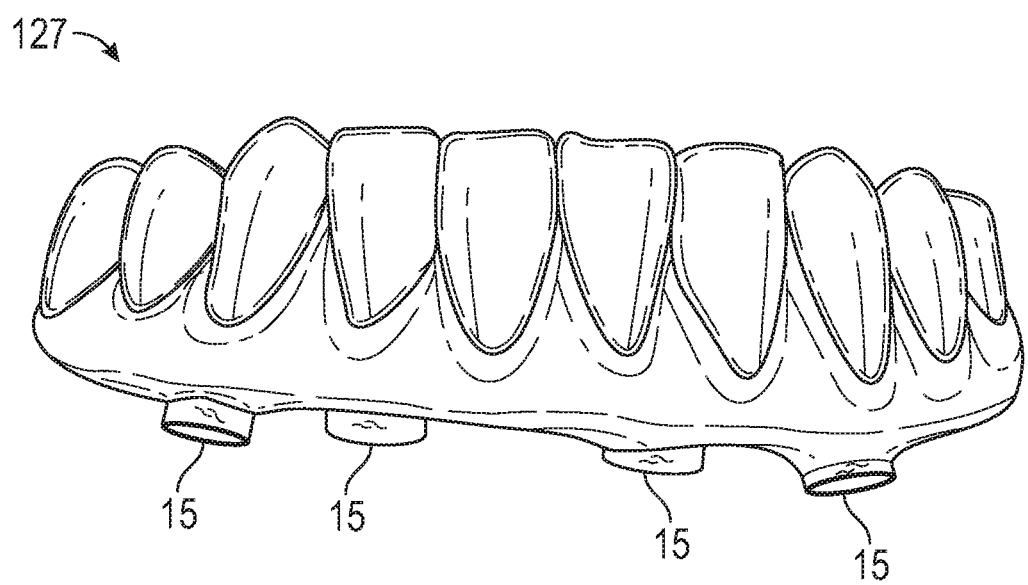
FIG. 27 shows a contrasting image from another patient showing a close-up view of the finished implant bridge of FIG. 26 that shows the scratches and damage on the cuff portions from attempts by the technician to remove residual resin while finishing and polishing; the use of the exemplary analog members with cuff protectors could have prevented this damage; these scratches can become a bacterial and/or plaque trap especially during healing from implant surgery; additionally, use of analog members with cuff protectors (FIGS. 13 and 14) would have made finishing and polishing procedures easier.

FIG. 27 shows a contrasting image from another patient showing a close-up view of the finished implant bridge 127 of FIG. 26 that shows the scratches and damage on the cuff portions 15 from attempts by the technician to remove residual resin 17 while finishing and polishing. The use of the exemplary analog members 10 or 100 with extending collar portions 14, 114 could have prevented this damage. These scratches on cuff portions 15 from FIG. 27 can become a bacterial and/or plaque trap especially during healing from implant surgery. Additionally, use of analog members with extending collar portions 14, 114 would have made finishing and polishing procedures easier.

While the present disclosure has been described with reference to preferred embodiments, it will be understood by those skilled in the art that various changes may be made and equivalents may be substituted for the elements thereof without departing from the scope of the present disclosure. In addition, many modifications may be made to adapt the teaching of the present disclosure to particular use, application, manufacturing conditions, use conditions, composition, medium, size, and/or materials without departing from the essential scope of the present disclosure. Therefore, it is intended that the present disclosure not be limited to the particular embodiments and best mode contemplated for carrying out this present disclosure as described herein.

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting of the true scope of the present disclosure disclosed herein. It is also to be understood that the terminology used herein is for the purpose of describing particular embodiments only, and is not intended to be limiting. Since many modifications, variations, and changes in detail can be made to the described examples, it is intended that the matters in the preceding description and shown in the accompanying figures be interpreted as illustrative and not in a limiting sense.

The ranges disclosed herein are inclusive of the endpoints, and the endpoints are independently combinable with each other. Each range disclosed herein constitutes a disclosure of a point or sub-range lying within the disclosed range.

The use of the terms "a" and "an" and "the" and words of a similar nature in the context of describing the improvements disclosed herein (especially in the context of the following claims) are to be construed to cover both the singular and the plural, unless otherwise indicated herein or clearly contradicted by context. Further, it should further be noted that the terms "first," "second," and the like herein do not denote any order, quantity, or relative importance, but rather are used to distinguish one element from another. The modifier "about" used in connection with a quantity is inclusive of the stated value and has the meaning dictated by the context (e.g., it includes, at a minimum the degree of error associated with measurement of the particular quantity).

The methods described herein can be performed in any suitable order unless otherwise indicated herein or otherwise clearly contradicted by context. The use of the examples, or exemplary language (e.g., "such as"), is intended merely to better illustrate the present disclosure and does not pose a limitation on the scope of the present disclosure or any embodiments unless otherwise claimed.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A dental analog member comprising:
a body that extends from a first end to a second end, the second end including a mounting member configured to mount to a mounting end of a coping member, the mounting end of the coping member including a cuff portion that extends from a first end to a second end;
an extending collar portion of the body that extends from a first end to a second end, the extending collar portion positioned: (i) proximal to the mounting member of the second end of the body and (ii) a distance between the first and second ends of the body, with at least a portion of the mounting member extending beyond the second end of the extending collar portion and toward the second end of the body to define the second end of the body;
wherein after the mounting member of the second end of the body is mounted to the mounting end of the coping member, the extending collar portion houses and covers the cuff portion of the coping member, the cuff portion having the largest outer diameter of the coping member.

2. The member of claim 1, wherein the mounting member of the second end of the body is a convex mounting member; and
wherein the mounting end of the coping member includes a concave mounting end.

3. The member of claim 1, wherein the first end of the body includes a dental abutment feature or dimension.

4. The member of claim 1, wherein the extending collar portion substantially matches the dimensions of the cuff portion of the coping member.

5. The member of claim 1, wherein after the extending collar portion houses and covers the cuff portion of the coping member, the extending collar portion prevents resin added during a fabrication process from adhering to the cuff portion of the coping member.

6. The member of claim 1, wherein the first end of the extending collar portion is positioned proximal to an interior abutment surface of the body, the interior abutment surface configured to abut against the first end of the cuff portion when the mounting member of the second end of the body is mounted to the mounting end of the coping member.

7. The member of claim 1, wherein the extending collar portion defines a protective receiving cavity configured to house the cuff portion of the coping member.

8. The member of claim 7, wherein the protective receiving cavity is defined between the extending collar portion and the mounting member of the second end of the body.

9. The member of claim 8, wherein the protective receiving cavity is configured to house or contain the cuff portion between the extending collar portion and the mounting member, and is configured to house or contain the cuff portion between the first and second ends of the extending collar portion.

10. The member of claim 1, wherein the extending collar portion is removable or replaceable relative to the body.

11. A method for utilizing a dental analog member comprising:
providing a body that extends from a first end to a second end, the second end including a mounting member, the body having an extending collar portion that extends from a first end to a second end, the extending collar portion positioned: (i) proximal to the mounting member of the second end of the body and (ii) a distance between the first and second ends of the body, with at least a portion of the mounting member extending beyond the second end of the extending collar portion and toward the second end of the body to define the second end of the body;
providing a coping member having a mounting end, the mounting end of the coping member including a cuff portion that extends from a first end to a second end;
mounting the mounting member of the second end of the body to the mounting end of the coping member;
wherein after the mounting member of the second end of the body is mounted to the mounting end of the coping member, the extending collar portion houses and covers the cuff portion of the coping member, the cuff portion having the largest outer diameter of the coping member.

12. The method of claim 11, wherein the mounting member of the second end of the body is a convex mounting member; and
wherein the mounting end of the coping member includes a concave mounting end.

13. The method of claim 11, wherein the first end of the body includes a dental abutment feature or dimension.

14. The method of claim 11, wherein the extending collar portion substantially matches the dimensions of the cuff portion of the coping member.

15. The method of claim 11, wherein after the extending collar portion houses and covers the cuff portion of the coping member, the extending collar portion prevents resin added during a fabrication process from adhering to the cuff portion of the coping member.

16. The method of claim 11, wherein the first end of the extending collar portion is positioned proximal to an interior abutment surface of the body, the interior abutment surface configured to abut against the first end of the cuff portion when the mounting member of the second end of the body is mounted to the mounting end of the coping member.

17. The method of claim 11, wherein the extending collar portion defines a protective receiving cavity configured to house the cuff portion of the coping member; and
wherein the protective receiving cavity is defined between the extending collar portion and the mounting member of the second end of the body.

18. The method of claim 17, wherein the protective receiving cavity is configured to house or contain the cuff portion between the extending collar portion and the mounting member, and is configured to house or contain the cuff portion between the first and second ends of the extending collar portion.

19. The method of claim 11, wherein the extending collar portion is removable or replaceable relative to the body.

20. A dental analog member comprising:
a body that extends from a first end to a second end, the second end including a convex mounting member configured to mount to a concave mounting end of a coping member, the concave mounting end of the coping member including a cuff portion that extends from a first end to a second end;
an extending collar portion of the body that extends from a first end to a second end, the extending collar portion positioned: (i) proximal to the convex mounting member of the second end of the body and (ii) a distance between the first and second ends of the body, with at least a portion of the mounting member extending beyond the second end of the extending collar portion and toward the second end of the body to define the second end of the body;
wherein after the convex mounting member of the second end of the body is mounted to the concave mounting end of the coping member, the extending collar portion houses and covers the cuff portion of the coping member, the cuff portion having the largest outer diameter of the coping member;
wherein after the extending collar portion houses and covers the cuff portion of the coping member, the extending collar portion prevents resin added during a fabrication process from adhering to the cuff portion of the coping member;
wherein the first end of the extending collar portion is positioned proximal to an interior abutment surface of the body, the interior abutment surface configured to abut against the first end of the cuff portion when the convex mounting member of the second end of the body is mounted to the concave mounting end of the coping member;
wherein the extending collar portion defines a protective receiving cavity configured to house the cuff portion of the coping member;
wherein the protective receiving cavity is defined between the extending collar portion and the convex mounting member of the second end of the body; and
wherein the protective receiving cavity is configured to house or contain the cuff portion between the extending collar portion and the convex mounting member, and is configured to house or contain the cuff portion between the first and second ends of the extending collar portion.

* * * * *